United States Patent [19]

Steinmetzer

[11] 4,263,450
[45] Apr. 21, 1981

[54] PROCESS FOR SEPARATING LEUCINE, ISOLEUCINE AND VALINE

[75] Inventor: Walter Steinmetzer, Süpplingen, Fed. Rep. of Germany

[73] Assignee: Societe d'Assistance Technique pour Produits Nestle S.A., Lausanne, Switzerland

[21] Appl. No.: 169,229

[22] Filed: Jul. 15, 1980

[30] Foreign Application Priority Data

Jul. 19, 1979 [EP] European Pat. Off. ........ 79102545.5

[51] Int. Cl.³ ............................................. C07C 99/12
[52] U.S. Cl. .................................................. 562/554
[58] Field of Search ............................... 562/554, 575

[56] References Cited

U.S. PATENT DOCUMENTS

| | | | |
|---|---|---|---|
| 2,471,053 | 2/1946 | Almquist | 562/554 |
| 3,433,832 | 3/1969 | Swanson | 562/554 |

FOREIGN PATENT DOCUMENTS

39-17811  8/1964  Japan ....................................... 562/554

OTHER PUBLICATIONS

Tsuchiya, Chem. Abst., 48:11,737b, (1953).
Vobayashi, Chem. Abst., 61:12084g, (1964).
Hamaguchi, Chem. Abst., 81:169839p, (1974).

*Primary Examiner*—Natalie Trousof
*Assistant Examiner*—Michael Shippen
*Attorney, Agent, or Firm*—Watson, Leavenworth, Kelton & Taggart

[57] ABSTRACT

A solution of leucine, isoleucine and valine is concentrated at a pH-value of from 1.5 to 2.0 to produce a mother liquor enriched with isoleucine and valine and a solid phase enriched with leucine. Concentrated hydrochloric acid is added to the mother liquor enriched with isoleucine and valine and, after concentration, a mother liquor enriched with valine and leucine and a solid phase enriched with isoleucine are obtained.

4 Claims, No Drawings

PROCESS FOR SEPARATING LEUCINE, ISOLEUCINE AND VALINE

This invention relates to a process for the separation of leucine, isoleucine and valine.

The amino acids leucine, isoleucine and valine have branched aliphatic side chains as a common structural feature. Due to these similar structural features, these amino acids are very similar in their physical and chemical behaviour and are extremely difficult to separate. Leucine, isoleucine and valine were separated for the first time through the copper complexes. In this process, the dried copper complexes of the amino acids are extracted with methanol, the copper salts of isoleucine and valine passing into solution. The further separation of valine and isoleucine follows a very complicated path on the lines of alkaline racemisation. In similar processes, the cobalt complexes of the amino acids are also separated by extraction with alcohol. In addition to the difficult separation of valine and isoleucine, these processes are beset by problems in the recovery of the metals and in the further purification of the amino acids.

In other processes, leucine is precipitated with aromatic sulphonic acids. Thus, the use of 2-bromotoluene-5-sulphonic acid and naphthalene-2-sulphonic acid has been proposed for the precipitation of leucine whilst the use of 1-chloro-naphthalene-4-sulphonic acid or 2-naphthol-6-sulphonic acid has been proposed for the precipitation of isoleucine. In these processes, the precipitates have to be purified by numerous recrystallisations and a particular problem is involved in separating off the often highly toxic precipitants and the valine which crystallises out together with the isoleucine.

The object of the present invention is to provide a new simple process for the separation of the amino acids leucine, isoleucine and valine in which no toxic or aggressive precipitants are used. The process according to the invention is based on a step-by-step enrichment of isoleucine and valine in the mother liquors during the crystallisation of leucine at pH-values in the range from 1.5 to 2.0 and on a reversal of this ratio by crystallising isoleucine hydrochloride from concentrated, preferably 20–30% hydrochloric acid and enriching leucine in the mother liquors.

By virtue of this reversal of the solubility behaviour of leucine, isoleucine and valine in the two different systems, which was found after exhaustive tests, these amino acids are separated by simple fractional crystallisation. To prepare the pure amino acids, the amino acid hydrochlorides dissolved in water may be treated with a weakly basic anion exchanger and the hydrochloric acid removed. The pure amino acids subsequently crystallise out on concentration of the neutral solutions.

Virtually any solution of the type which occurs in practice in the recovery of amino acids from a variety of protein sources such as, for example, desugared molasses, cereal or corn germs, oil press cake, micro-organisms, particularly yeasts or casein, and which mainly contain leucine, isoleucine and valine may be used as starting material for carrying out this new separation process. The preferred starting material is the amino acid solution described in German Patent Application No. 29 06 034 which has been freed from phenylalanine and tyrosine by treatment with a strongly basic anion exchanger.

The solution in question may be adjusted to a pH-value of from 1.0 to 2.0 with hydrochloric acid and concentrated. On concentration, a solid phase enriched with leucine crystallises out, whilst the mother liquors become enriched with isoleucine and valine. The leucine-rich solid phase may be separated off and another leucine-rich solid phase may be obtained by re-concentrating the mother liquor at a pH-value in the range from 1.0 to 2.0, whilst the mother liquor becomes enriched to an even greater extent with isoleucine and valine. The leucine-rich solid phase accumulating in the second stage may be returned to the preceding crystallisation stage or may be dissolved in water in order to crystallise out a purer leucine fraction at a pH-value in the range from 1.5 to 2.0. By repeating this operation, pure L-leucine may be obtained as solid phase. Equal parts of concentrated hydrochloric acid may be added to the mother liquors enriched with isoleucine and valine, followed by concentration. The quantity of hydrochloric acid used may be so large that, on concentration, an azeotropic mixture of hydrochloric acid and water, i.e. 21% hydrochloric acid, is ultimately obtained. When the hydrochloric acid solution is cooled, an enriched isoleucine hydrochloride crystallises out as solid phase, whilst the mother liquor becomes enriched with valine and leucine hydrochloride. By repeating the crystallisation process, i.e. by dissolving the isoleucine hydrochloride in 20 to 30% hydrochloric acid at 60° to 70° C., followed by crystallisation, it is possible further to purify the isoleucine hydrochloride.

These various crystallisation processes accompanied by recycling of mother liquors or solid phases are preferably repeated until the required purity of leucine and isoleucine is reached.

The free amino acids are preferably recovered from the amino acid hydrochlorides by treatment with weakly basic anion exchangers. The valine is enriched in the mother liquor from crystallisation of the isoleucine hydrochloride. The mother liquor may be concentrated and, after the addition of butanol or isobutanol, the amino acids may be esterified. During esterification, the water may be azeotropically distilled off by boiling under reflux, leaving a very high yield of amino acid esters. On completion of esterification, the amino acid ester hydrochlorides may be neutralised with sodium hydroxide and, after separation of the aqueous phase, the amino acid esters dissolved in the butanol may be separated by fractional distillation. Thus, the isobutyl ester of valine may be distilled off under a pressure of 3 mbar at 65° C., whilst the butyl esters of leucine and isoleucine are obtained as distillation residue. The amino acid esters may then be hydrolysed with 6 N hydrochloric acid by boiling under reflux and, by concentrating the hydrochloric acid solution, it is possible to crystallise out the respective hydrochlorides of the amino acids. The hydrochlorides of leucine and isoleucine obtained from the distillation residue may be returned to the separation process described above, whilst the valine hydrochloride may be dissolved in water and the hydrochloric acid separated off using a weakly basic anion exchanger. Pure valine crystallises out on concentration of the neutral solution.

The invention is illustrated by the following Examples in which the percentages quoted represent percent by weight.

EXAMPLE 1

Starting with a solution containing 0.7 part of isoleucine and 0.17 part of valine to 1 part of leucine, a solid phase A containing 0.3 and a mother liquor A' containing 1.1 parts of isoleucine to 1 part of leucine are obtained by concentration and crystallisation at pH 1.7. Further concentration of the mother liquor A' at pH 1.7 gives a solid phase B containing 0.5 part of isoleucine and a mother liquor B' containing 2.5 parts of isoleucine. This mother liquor B' is re-concentrated and crystallised, giving a solid phase C containing 1.0 part of isoleucine and a mother liquor C' containing 4.0 parts of isoleucine. 30% hydrochloric acid is added to mother liquor C' in a ratio of 1:1, followed by concentration. A solid phase D containing 7.2 parts of isoleucine crystallises out on cooling whilst the mother liquor D' contains 1.8 parts of isoleucine, based on leucine, i.e. the solubility ratios are reversed. The solid phase D is dissolved in 6 N hydrochloric acid at 70° C. A solid phase E containing 24 parts of isoleucine crystallises out on cooling whilst the mother liquor E' contains 2.7 parts of isoleucine.

The respective isoleucine, leucine and valine contents of the solid phases A, B, C, D and E and of the mother liquors A', B', C', D' amd E', expressed in an arbitrary unit of weight, are shown in the following Table. This Table clearly shows the distribution of the valine, based on isoleucine. In the first stages A, B and C, the L-valine becomes enriched with the isoleucine in the mother liquors and, on crystallisation from 6 N hydrochloric acid, isoleucine and valine are subsequently separated by the enrichment of valine in the mother liquor and enrichment of the isoleucine in the solid phases of stages D and E.

| Stage | Isoleucine | Leucine | Valine |
|---|---|---|---|
| Starting solution | 100 | 140 | 24 |
| A | 20 | 67 | 1.5 |
| A' | 80 | 73 | 22.5 |
| B | 25 | 50 | 3.7 |
| B' | 55 | 22 | 19 |
| C | 10 | 10 | 2 |
| C' | 45 | 12 | 16 |
| D | 28 | 4 | 4.5 |
| D' | 17 | 9 | 12.5 |
| E | 19 | 0.8 | 0.5 |
| E' | 9 | 3.2 | 3.5 |

EXAMPLE 2

2000 ml of an amino acid solution containing 90 g of leucine, 70 g of isoleucine and 20 g of valine are adjusted with hydrochloric acid to a pH-value of 1.9 and concentrated to approximately 1000 ml in a vacuum evaporator. After cooling, a solid phase containing 50 g of leucine, 10 g of isoleucine and 1 g of valine is obtained, whilst 40 g of leucine, 60 g of isoleucine and 19 g of valine remain in the mother liquor. After separation of the leucine fraction, the mother liquor is re-concentrated and another leucine residue is obtained, being used at the beginning of the process in the next cycle. The mother liquor from the second crystallisation contains 20 g of leucine, 50 g of isoleucine and 17 g of valine. After addition of the same quantity of 20% hydrochloric acid, this mother liquor is concentrated in vacuo. An isoleucine hydrochloride with a purity of 80% crystallises out after cooling. This isoleucine hydrochloride is dissolved in the same quantity of 20% hydrochloric acid at 70° C. Isoleucine hydrochloride again crystallises out after cooling. This isoleucine hydrochloride has a purity of as high as 95 to 98%.

EXAMPLE 3

After two crystallisation steps at pH 1.9 and two crystallisation steps from 20% hydrochloric acid, a mother liquor from the precipitation of isoleucine hydrochloride containing 10% of valine, 7% of isoleucine and 7% of leucine is obtained. Isobutanol is added to this mother liquor in a ratio of 1:1, followed by esterification for 24 hours by boiling under reflux with continuous separation of the water distilled over. On completion of esterification, the solution of the ester hydrochlorides is neutralised with dilute sodium hydroxide and the aqueous phase is separated off. The free amino acid isobutyl esters are contained in the butanol phase. The excess butyl alcohol is distilled off in vacuo, after which the valine ester is separated off from the leucine and isoleucine ester by fractional distillation. Under a pressure of 3 mbar, the isobutyl ester of valine boils at 65° C. The valine isobutyl ester distilled off is boiled under reflux for 3 hours with twice the quantity of 6 N hydrochloric acid and subsequently concentrated in vacuo, after which the pure valine hydrochloride which has crystallised out is separated off.

EXAMPLE 4

200 g of an isoleucine hydrochloride obtained as described in Example 2 are dissolved in 2 liters of water and the resulting solution is passed through an exchanger column containing 1 liter of a weakly basic anion exchanger at a rate of 2 bed volumes per hour. The column is then washed with water and the outflow containing washing water is concentrated in vacuo. After cooling, the pure isoleucine which has crystallised out is separated off and dried.

We claim:

1. A process for the separation of leucine, isoleucine and valine which comprises concentrating a solution of these three amino acids at a pH-value of from 1.5 to 2.0 to produce a first mother liquor, enriched with isoleucine and valine and a first solid phase, enriched with leucine, and separating the mother liquor from the solid phase.

2. A process according to claim 1 which further comprises adding hydrochloric acid to the mother liquor enriched with isoleucine and valine, concentrating the mother liquor to produce a second mother liquor, enriched with valine and leucine, and a second solid phase, enriched with isoleucine, and separating the second mother liquor from the second solid phase.

3. A process according to claim 2 in which prior to the addition of hydrochloric acid the mother liquor is concentrated at least twice, a solid phase being separated after each concentration step.

4. A process according to claim 2 or claim 3 which further comprises treating amino acid hydrochlorides formed upon addition of hydrochloric acid with a weakly basic ion exchanger and recovering free amino acids thus liberated.

* * * * *